United States Patent
Lienard et al.

(10) Patent No.: US 7,343,029 B2
(45) Date of Patent: Mar. 11, 2008

(54) PROCESS AND DEVICE FOR VASCULAR NAVIGATION

(75) Inventors: Jean Lienard, Igny (FR); Daniel Gannat, Montigny le Bretonneux (FR); Julien Leger, Paris (FR)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 644 days.

(21) Appl. No.: 10/742,340

(22) Filed: Dec. 19, 2003

(65) Prior Publication Data

US 2006/0241369 A1    Oct. 26, 2006

(30) Foreign Application Priority Data

Dec. 20, 2002  (FR) .................................. 02 16286

(51) Int. Cl.
*G06K 9/00*  (2006.01)
(52) U.S. Cl. ........................... 382/128; 128/922; 378/4
(58) Field of Classification Search ................ 382/100, 382/128, 130, 131; 128/922; 378/4
See application file for complete search history.

(56) References Cited

U.S. PATENT DOCUMENTS 5,802,133 A * 9/1998 Kawai et al. ................... 378/4
6,370,417 B1 * 4/2002 Horbaschek et al. ......... 600/424
6,643,533 B2 * 11/2003 Knoplioch et al. .......... 600/407
6,711,433 B1 * 3/2004 Geiger et al. ................ 600/431
6,842,638 B1 * 1/2005 Suri et al. .................... 600/425
6,993,374 B2 * 1/2006 Sasso .......................... 600/426
2001/0036302 A1 * 11/2001 Miller .......................... 382/128
2005/0018885 A1 * 1/2005 Chen et al. .................. 382/128

FOREIGN PATENT DOCUMENTS

EP    0463 533 A1    1/1992
EP    0515 282 A1    12/1992

* cited by examiner

*Primary Examiner*—Bhavesh M. Mehta
*Assistant Examiner*—Anand Bhatnagar
(74) *Attorney, Agent, or Firm*—Cantor Colburn LLP (57) ABSTRACT

A process and radiography device for aiding vascular navigation suitable for an area of interest wherein a series of successive images $I_n$ of the region of interest is acquired by a image recording. From the series of images $I_n$ thus acquired a determination is made of a first mask presenting background structures and blood vessels of the region of interest, and a second mask presenting the only background structures. An image $I_L$ is acquired exhibiting at least one instrument introduced into one of the vessels of the region of interest. An image $I_v$ is determined for visualizing by combination of the first and second masks and the image. The image to be visualized thus determined is displayed.

34 Claims, 5 Drawing Sheets

FIG_1

FIG_4

FIG_5

FIG_6

ND DEVICE FOR VASCULAR
PROCESS AND DEVICE FOR VASCULAR NAVIGATION

CROSS-REFERENCE TO RELATED APPLICATIONS

This application claims a benefit of a priority under 35 USC 119(a)-(d) to French Patent Application No. 02 16286 filed Dec. 20, 2002, the entire contents of which are hereby incorporated by reference.

BACKGROUND OF THE INVENTION

This invention relates to a process and device for vascular navigation intended for a radiological imaging device and more particular to an X-ray fluoroscopy device.

Figure 1:
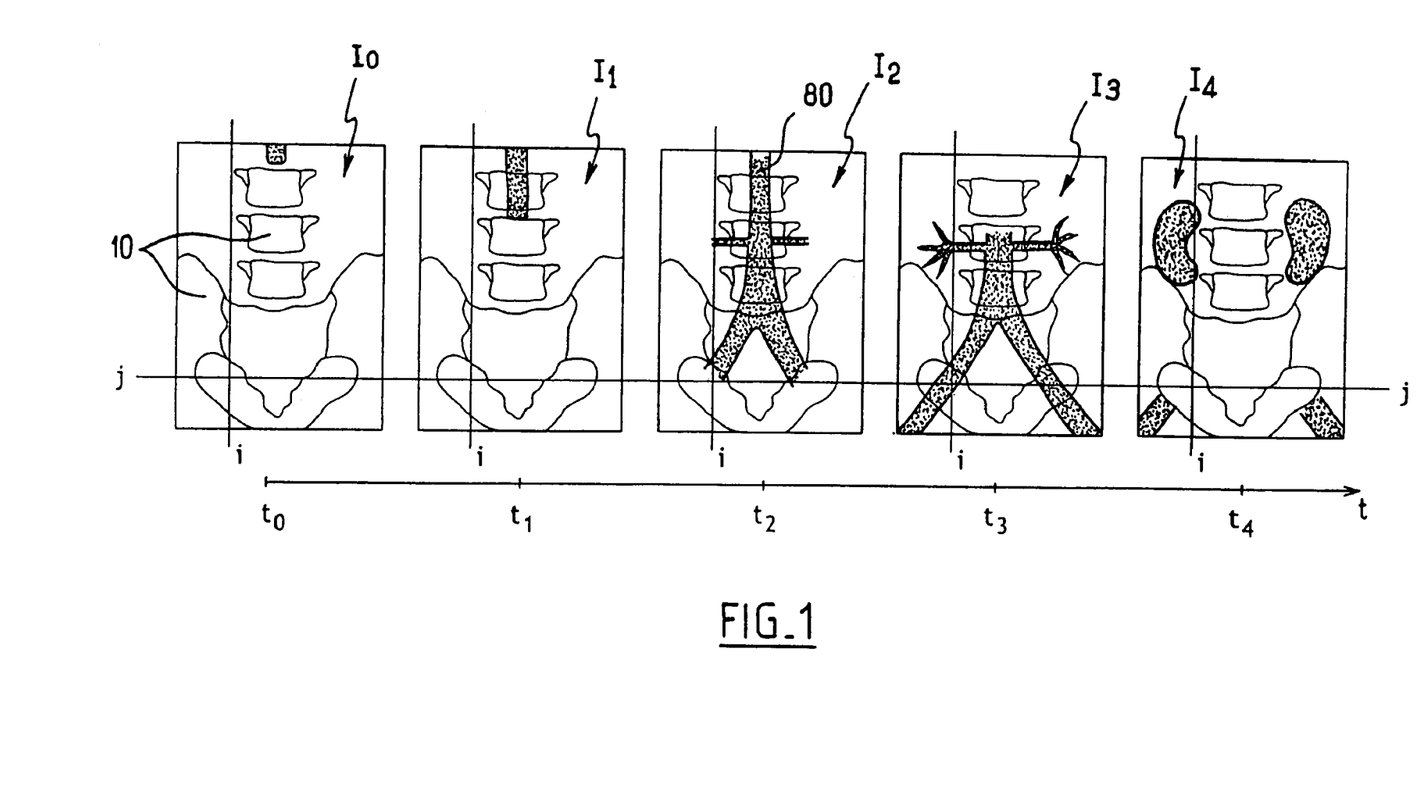
FIG. 1 is a series of images acquired when a contrast product is injected, serving as input data in an embodiment of the process.

Process for vascular navigation enable a map to be drawn up of the blood vessels of an area of interest of a patient faced with surgery. During vascular surgery the surgeon inserts devices and tools (guide, catheter, stents, etc) into the blood vessels and moves them to where the lesion needs to be treated. For this the surgeon uses the previously created map of the vessels as a guide by injecting contrast products into the vessels to be X-rayed and by simultaneous acquisition of a sequence of images showing progressive opacification of the vessels, as illustrated in FIG. 1. The entire sequence is then treated by well-known image treatment techniques, such as the maximum opacification technique. The drawback to this technique is that the vascular map always contains the bones and soft tissue (forming said background structures) that can more or less hide parts of the blood vessels on account of their possible high absorption of X-rays. In the event where this particular map is subtracted from a fluoroscopic image taken during the intervention, the vessels and background structures are treated in the same manner, and the operator or medical practitioner may be uncertain of the route to follow by these instruments, or of their position. This is prejudicial for patients due to error causes this may contribute and by prolonging operating times.

BRIEF DESCRIPTION OF THE INVENTION

An embodiment of the invention is to provide a process and device for vascular navigation that may resolve the above mentioned problems. An embodiment of the invention and equivalents provides a process and a device for vascular navigation intended for a radiography/fluoroscopy device. The device may comprise means for emitting radiation, such as a source of X-rays; means for recording or acquiring an image arranged opposite the source and means for support arranged between the source and the means for recording on which a patient with an area or region of interest to be imaged is intended to be placed. The process comprises: acquiring a senses of successive images of the region of interest by the means for recording; determining from the series of images thus acquired a first mask presenting background structures and blood vessels of a region of interest; presenting a second mask of only the background structure; acquiring an image exhibiting at least one instrument introduced into one of the vessels in the region of interest, determining an image for visualizing by combining the first and second masks and the image; and displaying the image to be visualized thus determined on means for display.

BRIEF DESCRIPTION OF THE DRAWINGS

An embodiment of the invention will be better understood from the following description when read together with the attached drawings, in which.

DETAILED DESCRIPTION OF THE INVENTION

Figure 6:
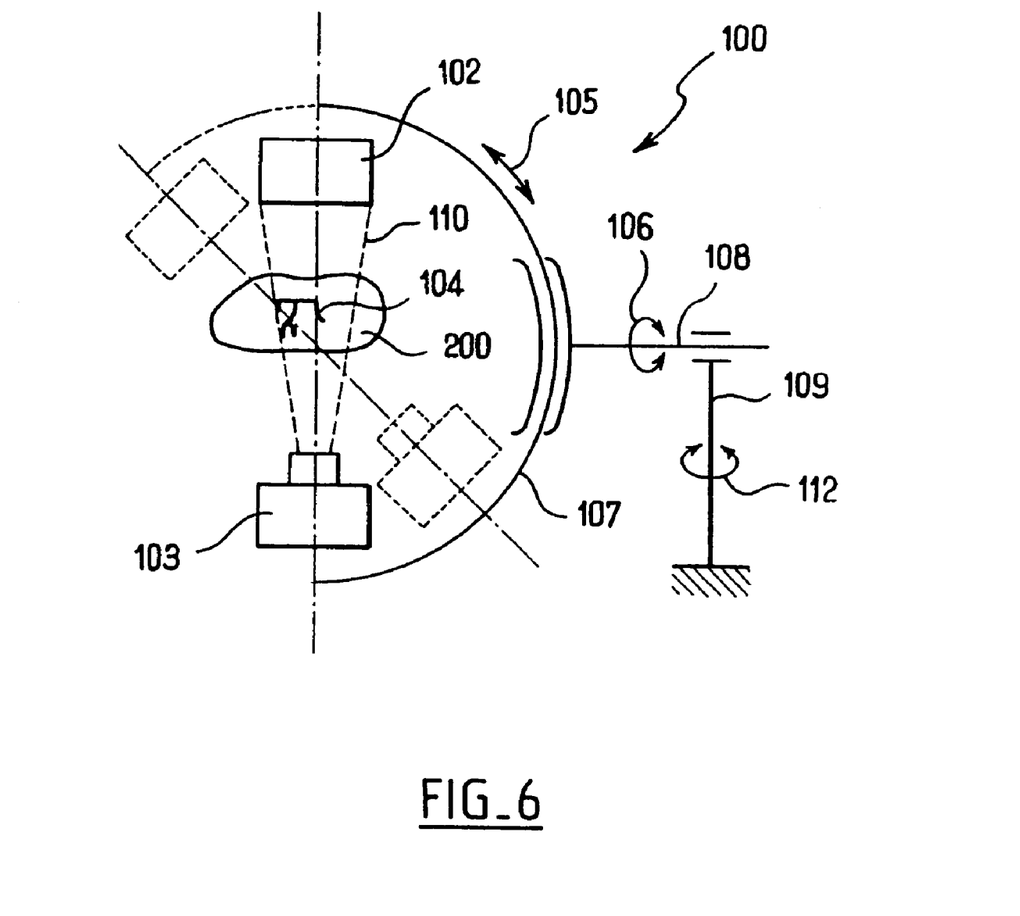
FIG. 6 is a diagram of a radiography device suitable for implementing an embodiment of the process.

FIG. 6 shows an embodiment of a radiography device 100. The device comprises means for recording or acquiring images, such as X-ray plates 102, and means for emitting radiation 103 in the form of a source of X-rays. The means for recording or acquiring images 102 can be a flat probe or a brightness amplifier linked to a camera. The means for emitting radiation 103 and the means for recording or acquiring images 102 are fixed at each end of a carry arm 107 serving as balance counter, here resembling a semi-circle. The semi-circular arm 107 is slidably attached to a second arm 108. Second arm 108 is in turn rotatably attached to a base 109 of the device 100. Base 109 is mounted to rotate 112 relative to the ground.

Arm 108 is essentially suitable for carrying out movements of rotation 106 about its own axis. The semi-circular arm 107 is suitable to slide relative to the arm 108, such that the semi-circular arm 107 describes a movement of rotation relative to the center of the semi-circle forming the arm 107.

In use a body, such as a patient 200, is placed on a support (not shown) between the source 103 and the means for recording or acquiring images 102, so that a region of interest 104 of the patient 200 is located in a field 110 of the apparatus.

In FIG. 1 a first stage of the process for aiding navigation is the acquisition of a series of successive images $I_n$ of the region of interest 104 of the patient 200, whereas a contrast product has been injected into the blood vessels of the region of interest. In FIG. 1 illustrates a set of five successive images, numbered I0 to I4, showing the progression of the contrast product in the circulatory system 20 of the region of interest under the action of the blood circulation of the patient 200. In addition, the different images of the sequence presenting a set of so-called background structures 10 which correspond to all the tissue of the region of interest of the patient 200 other than the blood vessels. In FIG. 1 of the set of so-called background structures only the bones 10 have been shown.

A second stage the process of aiding navigation determines a first mask PO and a second mask M. The second stage can be taken simultaneously with acquiring the series of successive images previously described. In this case the series of images is not recorded in means for image storage of the device. Only the first and second masks are recorded in the means for storage.

Figure 2:
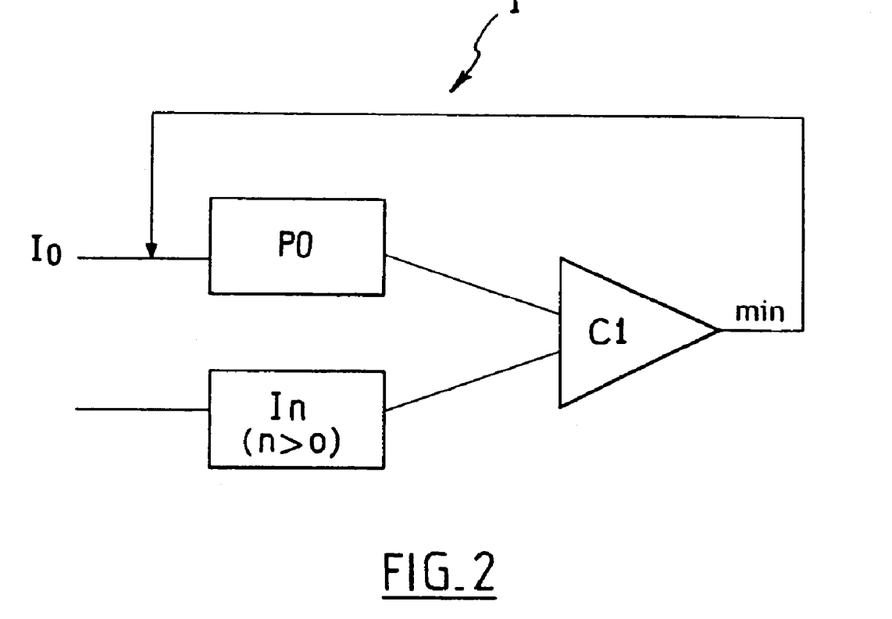
FIG. 2 is a diagram illustrating a first mask in an embodiment of the process.

In FIG. 2 the first mask PO is determined according to the maximum opacification 1. In the first instance the first mask PO is initialized with the content of the first image $I_0$ of the sequence of images previously acquired. Next, each point (i, j) of the image $I_n$ is compared to the corresponding point (i, j) of the first mask PO by looping on the set of other $I_n$ images of the image sequence. If the intensity of the point in question of the $I_n$ image is less than that of its equivalent on the mask PO, then the point of the mask PO is replaced by the point of the $I_n$ image. This operation is carried out for all points making up the $I_n$ image and for all the images of the series from the second image. A comparator C1 shown in FIG. 2 performs all of these operations.

Figure 3:
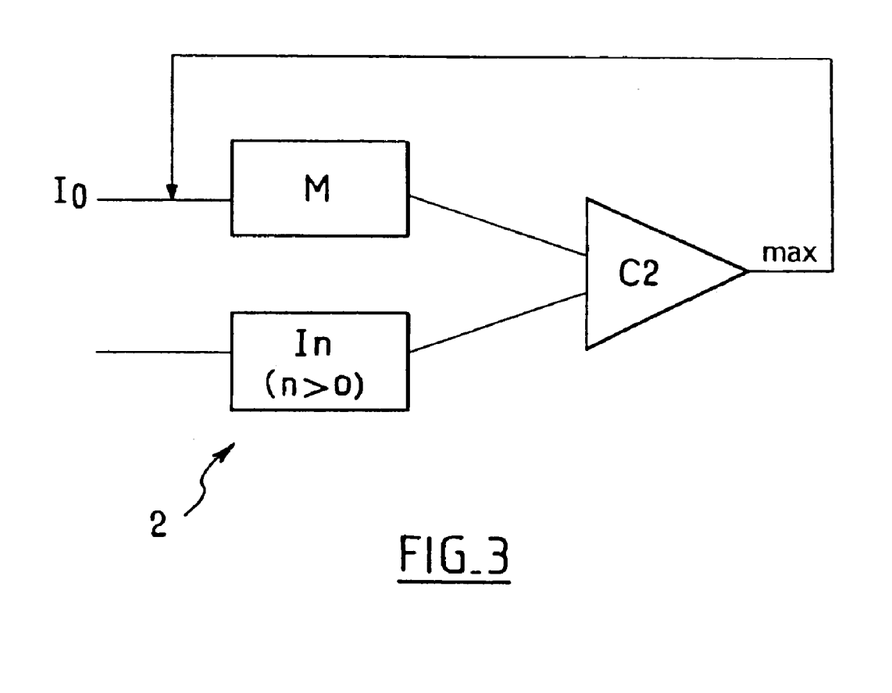
FIG. 3 is a diagram illustrating a second mask in an embodiment of the process.

In FIG. 3 a determination 2 of the second mask M is carried out relatively similarly to determining the first mask PO. In the first instance, the second mask M is initialised with the first image $I_n$ of the series of images previously acquired. Then, for each ensuing $I_n$ image of the series the intensity of the point (i, j) of the image $I_n$ is compared with the intensity of the corresponding point (i, j) of the second mask M, the point presenting the greatest intensity becoming the new point (i, j) of the second mask M. As before, this operation is performed for all points of the $I_n$ image and for all the images of the series from the second image.

Figure 4:
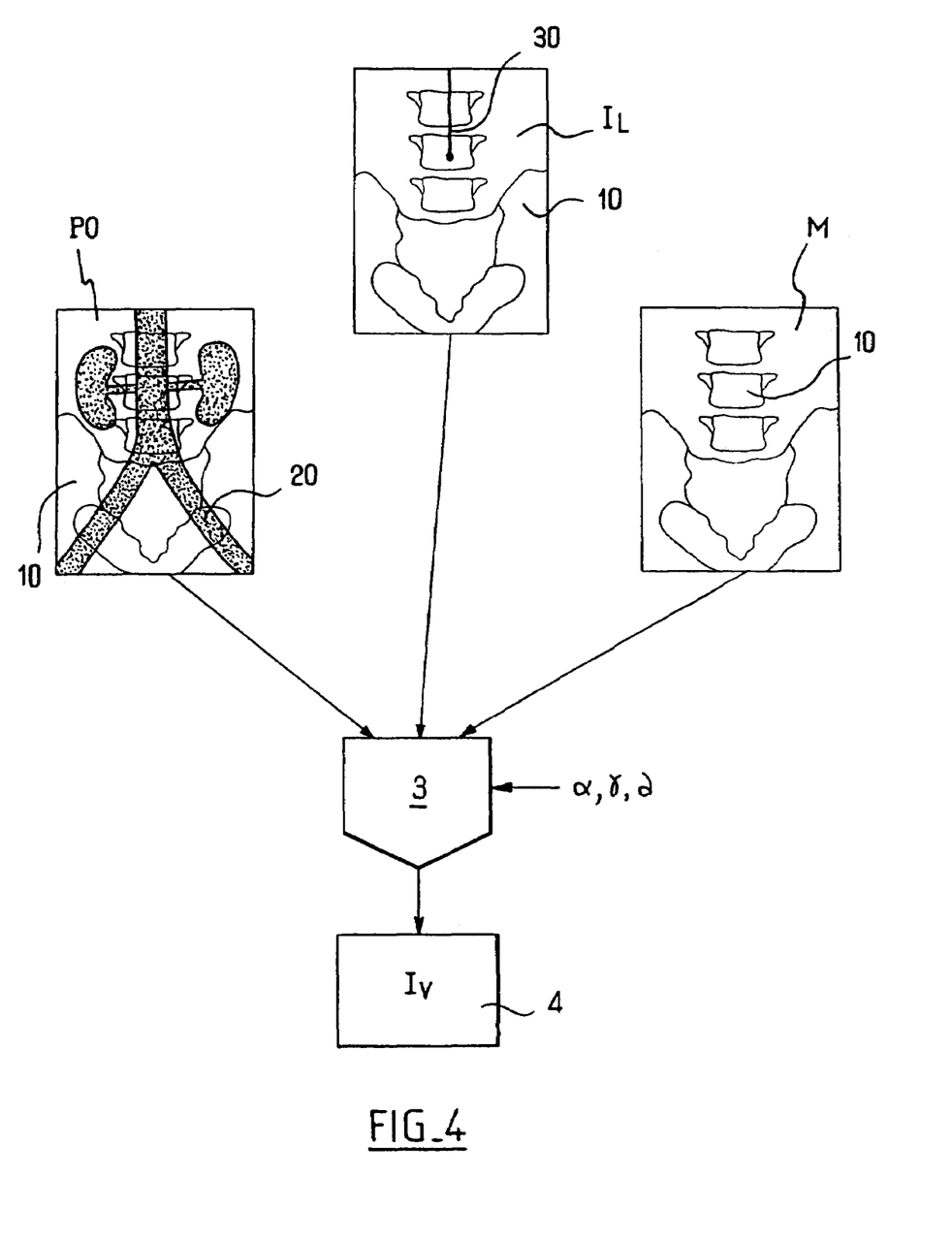
FIG. 4 is a diagram illustrating an image to be visualized in an embodiment of the process.

On completion of the second stage of the process a determination has been made of a first so-called maximum opacification mask PO at the same time presenting the blood vessels travelled through by the contrast products and the background structures, with an example of a result thus obtained illustrated in FIG. 4. Likewise, the process aiding navigation according to the present invention has determined a second so-called M mask of maximum intensity that shows the sole background structures (an example of which is illustrated in FIG. 4).

In a third stage, generally occurring during surgical intervention on the patient 200 in the region of interest 104, a sequence of live images $I_L$ is taken in fluoroscopy, while the surgeon inserts an instrument 30 into a blood vessel of the zone of interest 104. Such an image of this sequence is illustrated in FIG. 4.

If the second mask M is subtracted from the live image $I_L$, the result is an image representing the instrumentation 30 only; the second mask M allows the background structures of the live $I_L$ image to be deleted. On the other hand, if the first mask PO of the second mask M is subtracted the result is a vascular cartography/map showing only the set of blood vessels traversed by the contrast product; the elements common to both masks, that is, the background structures, are cancelled out.

So as to be able to situate instrument 30 the surgeon indicates three coefficients α, γ, λ that are actual positives for the process. These coefficients are weighting coefficients vis-a-vis the image representing just the instrumentation ($I_L$−M), just the vascular cartography/map (M−PO) and the second mask M, respectively. The weighting coefficients applied to the three images will allow an image $I_v$ to be visualized which the surgeon can have displayed by the device on means for display 4, in a sub-stage 3. The image $I_v$ to be visualized is equal to α times the instrumentation image only plus γ times the vascular map only plus λ times the second mask M. In a variant embodiment the coefficients α,γ,λ are actuals of between 0 and 1.

In another variant embodiment the value of these coefficients can be greater than 1 if the surgeon wants amplification on one or more of the three images. This addition operation with application of weighting coefficients is performed point by point.

In a variant embodiment the process does not actually calculate the instrumentation image only, not the vascular map image only. The process directly calculates:

$$I_v = \alpha(I_L - M) + \gamma(M - PO) + \lambda M = \alpha I_L + (\gamma + \lambda - \alpha)M - \gamma PO.$$

Figure 5:
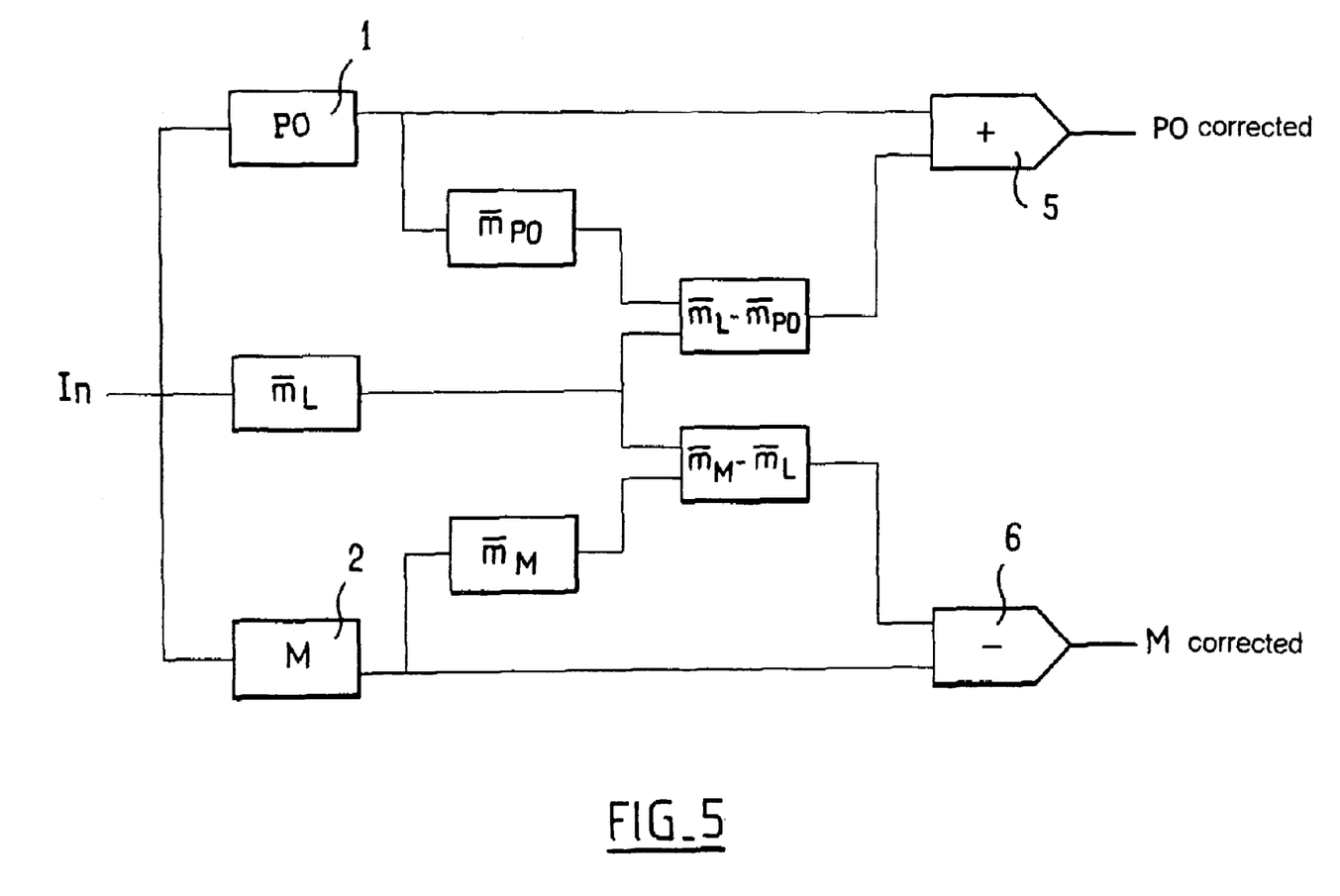
FIG. 5 is a diagram illustrating noise correction on images of an embodiment of the process.

FIG. 5 describes a correction stage for images included in a variant embodiment of the process. The set of images $I_n$ of the series of previously acquired images is not perfect and has noise that has to be corrected. Once the process has determined the first and second masks (PO, M), such as described earlier, the first and second masks are raw and take into consideration all the noise issuing from the series of images at the weakest amplitudes for the first mask and at the strongest amplitudes for the second mask. The average level of the masks thus calculated may be very different from one mask to the other. To correct this spread the process calculates an average intensity $\overline{m}_L$ that corresponds to the average intensity in the entire region of interest on the series of images, directly from the set of images $I_n$ of the series of images. Next, the process performs a similar calculation from the previously described first and second raw masks issuing from the second stage. In this way the process determines an average intensity $\overline{m}_{PO}$ concerning the first mask PO and an average intensity $\overline{m}_M$ for the second mask PO. Then, using the three calculated average intensity values, the process will correct the abovementioned first and second raw masks PO, M issued from sub-stages 1 and 2. In relation to the first mask PO in a sub-stage 5 the process will re-evaluate the intensity of all the points forming the first raw mask P of equal value $(\overline{m}_L - \overline{m}_{PO})$ approximately. The result is a corrected first mask PO. Similarly in a sub-stage 6 the process will devalue the intensity of all the points forming the second raw mask M of equal value $(\overline{m}_M - \overline{m}_L)$ approximately. The result is a corrected second mask M.

The two masks thus corrected serve as input data for the third abovementioned stage of the process enabling an image $I_v$ to be visualized to be determined.

For implementing the entire process it is understood that neither the patient 200 nor the arm 107 is supposed to move between the acquisition of all the images $I_n$ forming the series of images and the successive recordings at the discretion of the surgeon of live images $I_L$. However, if there is movement from either the patient 200 or the arm 107 then the process can automatically impose γ=0 and λ=1.

In a variant embodiment of the process the value of the three coefficients α,γ,λ live is memorized before displacement in the means for storage contained in the radiography device. Therefore, as soon as the device discovers the previous displacement position the process can again take up the same coefficient values to display the image to be visualized corresponding to this position. This return to the previous displacement position can be done automatically by the radiography device, thus ensuring perfect repositioning, such that the live images $I_L$ correspond exactly to the set of images $I_n$ of the series of images initially acquired. All the same, if the surgeon does this return it can be only approximated and the process makes an adjustment to the set of masks PO and M using known image verification techniques by point shift.

Consequently, the action of calculating a second mask exhibiting only the background structures enables the background structures to be subtracted from the image to be visualised and to have only the cartography/map of the blood vessels be legible by the operator while the instruments are being moved.

According to other embodiments the process presents at least one of the following characteristics:

The first mask is determined by:

initializing the mask with the first image of the series of acquired images;

for each following image of the series of images the intensity of each point (i, j) of the image of the series is compared to the intensity of the corresponding point (i, j) of the first mask, the least intense point (i, j) becoming the point (i, j) of the first mask.

The second mask is determined by:

initializing the second mask with the first image of the series;

for each following image of the series the intensity of the point (i, j) of the image of the series is compared to the intensity of the corresponding point (i, j) of the second mask, the least intense point (i, j) becoming the point (i, j) of the second mask.

The image to be determined by a live combination of the first and second masks and of the live image.

The image to be visualized is determined by a formula of the type $I_v = \alpha(I_L - M) + \gamma(M - PO) + \lambda M$ where $\alpha$, $\gamma$ and $\lambda$ are positive actuals; $I_L$ is the fluoroscopic image, PO is the first mask, M is the second mask, $(I_L - M)$ is the image representing the sole instrument and $(M - PO)$ is the image presenting the map of only the vessels.

While the masks are being determined the process comprises a process for correcting the noise present in the masks.

Correction comprises:

determining an average intensity mL in a region of interest from the series of images acquired earlier;

determining the first of raw second masks from the series of images acquired earlier;

determining an average intensity of the first and second raw masks, $m_{PO}$ and $m_M$ respectively, in respective regions of interest corresponding to that of the series of images acquired earlier;

correction of the first and second raw masks from average intensities $m_L$, $m_{PO}$, $m_M$ previously evaluated.

Each point of the first raw mask has an intensity re-evaluated by a value $(m_L - m_{PO})$ approximately, and each point of the second raw mask has an intensity devaluated by a value $(m_M - m_L)$ approximately.

One skilled in the art may make or proposed various modifications to the structure/way and/or function and/or result of the disclosed embodiments and equivalents thereof without departing from the scope and extant of the invention.

What is claimed is:

1. A process for aiding vascular navigation comprising:
  a. acquiring a series of successive images $(I_n)$ of a region of interest;
  b. determining from the series of images $(I_n)$ thus acquired a first mask presenting background structures and blood vessels of the region of interest;
  c. determining a second mask presenting only the background structures;
  d. acquiring an image $(I_L)$ exhibiting at least one instrument introduced into one of the vessels of the region of interest;
  e. determining an image $(I_v)$ for visualizing by combination of the first and second masks and the image exhibiting the at least one instrument; and
  f. displaying the image to be visualised thus determined.

2. The process as claimed in claim 1 wherein the combining is by subtraction.

3. The process as claimed in claim 2 wherein the second mask is determined by:

initializing the second mask with the first image $(I_0)$ of the series of images thus acquired;

for each following image $(I_n)$ of the series of images the intensity of the point (i, j) of the following image $(I_n)$ of the series is compared to the intensity of the corresponding point (i, j) of the second mask, the least intense point (i, j) becoming the point (i, j) of the second mask.

4. The process as claimed in claim 2 wherein the image to be visualized is determined by a weighted combination of the first and second masks and a live image.

5. The process as claimed in claim 2 wherein the image to be visualized is determined by a formula of the type $I_v = \alpha(I_L - M) + \gamma(M - PO) + \lambda M$ where $\alpha$, $\gamma$ and $\lambda$ are positive actuals, $I_L$ is the, PO is the first mask, M is the second mask, $(I_L - M)$ is the image representing just the instrument and $(M - PO)$ is the image presenting the map of only the vessels.

6. The process as claimed in claim 2 wherein when the masks are being determined the process comprises a correction stage for noise present in the masks.

7. The process as claimed in claim 6 wherein the correction comprises:

determining an average intensity $(m_L)$ of the region of interest from the series of images $(I_n)$ acquired earlier;

determining the first and second raw masks from the series of images acquired earlier;

determining an average intensity of the first and second raw masks, $(m_{PO}$ and $m_M)$ respectively; and correcting the first and second raw masks from the average intensities $(m_L, m_{PO}, m_M)$ previously calculated.

8. The process as claimed in claim 6 wherein during correction the intensity of each point of the first raw mask is re-evaluated by a value equivalent to $m_L - m_{PO}$ approximately and the intensity of each point of the second raw mask M is devalued by an equivalent value $m_M - m_L$ approximately.

9. The process as claimed in claim 1 wherein the first mask is determined by:

initializing the first mask with a first $(I_0)$ image of the acquired series of images; and for each following image $(I_n)$ of the series of images the intensity of each point (i, j) of the following image $(I_n)$ of the series is compared to the intensity of a corresponding point (i, j) of the first mask, a least intense point (i, j) becoming the point (i, j) of the first mask.

10. The process as claimed in claim 9 wherein the second mask is determined by:

initializing the second mask with the first image $(I_0)$ of the series of images thus acquired;

for each following image $(I_n)$ of the series of images the intensity of the point (i, j) of the following image $(I_n)$ of the series is compared to the intensity of the corresponding point (i, j) of the second mask, the least intense point (i, j) becoming the point (i, j) of the second mask.

11. The process as claimed in claim 9 wherein the image to be visualized is determined by a weighted combination of the first and second masks and a live image.

12. The process as claimed in claim 9 wherein the image to be visualized is determined by a formula of the type $I_v = \alpha(I_L - M) + \gamma(M - PO) + \lambda M$ where $\alpha$, $\gamma$ and $\lambda$ are positive actuals, $I_L$ is the, PO is the first mask, M is the second mask, $(I_L - M)$ is the image representing just the instrument and $(M - PO)$ is the image presenting the map of only the vessels.

13. The process as claimed in claim 9 wherein when the masks are being determined the process comprises a correction stage for noise present in the masks.

14. The process as claimed in claim 13 wherein the correction comprises:
   determining an average intensity ($m_L$) of the region of interest from the series of images ($I_n$) acquired earlier;
   determining the first and second raw masks from the series of images acquired earlier;
   determining an average intensity of the first and second raw masks, ($m_{PO}$ and $m_M$) respectively; and
   correcting the first and second raw masks from the average intensities ($m_L$, $m_{PO}$, $m_M$) previously calculated.

15. The process as claimed in claim 13 wherein during correction the intensity of each point of the first raw mask is re-evaluated by a value equivalent to $m_L-m_{PO}$ approximately and the intensity of each point of the second raw mask M is devalued by an equivalent value $m_M-m_L$ approximately.

16. The process as claimed in claim 1 wherein the second mask is determined by:
   initializing the second mask with the first image ($I_0$) of the series of images thus acquired;
   for each following image ($I_n$) of the series of images the intensity of the point (i, j) of the following image ($I_n$) of the series is compared to the intensity of the corresponding point (i, j) of the second mask, the least intense point (i, j) becoming the point (i, j) of the second mask.

17. The process as claimed in claim 16 wherein the image to be visualized is determined by a weighted combination of the first and second masks and a live image.

18. The process as claimed in claim 16 wherein the image to be visualized is determined by a formula of the type $I_v=\alpha(I_L-M)+\gamma(M-PO)+\lambda M$ where $\alpha$, $\gamma$ and $\lambda$ are positive actuals, $I_L$ is the, PO is the first mask, M is the second mask, ($I_L-M$) is the image representing just the instrument and (M-PO) is the image presenting the map of only the vessels.

19. The process as claimed in claim 18 wherein when the masks are being determined the process comprises a correction stage for noise present in the masks.

20. The process as claimed in claim 19 wherein the correction comprises:
   determining an average intensity ($m_L$) of the region of interest from the series of images ($I_n$) acquired earlier;
   determining the first and second raw masks from the series of images acquired earlier;
   determining an average intensity of the first and second raw masks, ($m_{PO}$ and $m_M$) respectively; and
   correcting the first and second raw masks from the average intensities ($m_L$, $m_{PO}$, $m_M$) previously calculated.

21. The process as claimed in claim 19 wherein during correction the intensity of each point of the first raw mask is re-evaluated by a value equivalent to $m_L-m_{PO}$ approximately and the intensity of each point of the second raw mask M is devalued by an equivalent value $m_M-m_L$ approximately.

22. The process as claimed in claim 16 wherein when the masks are being determined the process comprises a correction stage for noise present in the masks.

23. The process as claimed in claim 22 wherein the correction comprises:
   determining an average intensity ($m_L$) of the region of interest from the series of images ($I_n$) acquired earlier;
   determining the first and second raw masks from the series of images acquired earlier;
   determining an average intensity of the first and second raw masks, ($m_{PO}$ and $m_M$) respectively; and
   correcting the first and second raw masks from the average intensities ($m_L$, $m_{PO}$, $m_M$) previously calculated.

24. The process as claimed in claim 22 wherein during correction the intensity of each point of the first raw mask is re-evaluated by a value equivalent to $m_L-m_{PO}$ approximately and the intensity of each point of the second raw mask M is devalued by an equivalent value $m_M-m_L$ approximately.

25. The process as claimed in claim 1 wherein the image to be visualized is determined by a weighted combination of the first and second masks and a live image.

26. The process as claimed in claim 25 wherein the image to be visualized is determined by a formula of the type $I_v=\alpha(I_L-M)+\gamma(M-PO)+\lambda M$ where $\alpha$, $\gamma$ and $\lambda$ are positive actuals, $I_L$ is the, PO is the first mask, M is the second mask, ($I_L-M$) is the image representing just the instrument and (M-PO) is the image presenting the map of only the vessels.

27. The process as claimed in claim 25 wherein when the masks are being determined the process comprises a correction stage for noise present in the masks.

28. The process as claimed in claim 27 wherein the correction comprises:
   determining an average intensity ($m_L$) of the region of interest from the series of images ($I_n$) acquired earlier;
   determining the first and second raw masks from the series of images acquired earlier;
   determining an average intensity of the first and second raw masks, ($m_{PO}$ and $m_M$) respectively; and
   correcting the first and second raw masks from the average intensities ($m_L$, $m_{PO}$, $m_M$) previously calculated.

29. The process as claimed in claim 27 wherein during correction the intensity of each point of the first raw mask is re-evaluated by a value equivalent to $m_L-m_{PO}$ approximately and the intensity of each point of the second raw mask M is devalued by an equivalent value $m_M-m_L$ approximately.

30. The process as claimed in claim 1 wherein when the masks are being determined the process comprises a correction stage for noise present in the masks.

31. The process as claimed in claim 30 wherein the correction comprises:
   determining an average intensity ($m_L$) of the region of interest from the series of images ($I_n$) acquired earlier;
   determining the first and second raw masks from the series of images acquired earlier;
   determining an average intensity of the first and second raw masks, ($m_{PO}$ and $m_M$) respectively; and
   correcting the first and second raw masks from the average intensities ($m_L$, $m_{PO}$, $m_M$) previously calculated.

32. The process as claimed in claim 31 wherein during correction the intensity of each point of the first raw mask is re-evaluated by a value equivalent to $m_L-m_{PO}$ approximately and the intensity of each point of the second raw mask M is devalued by an equivalent value $m_M-m_L$ approximately.

33. The process as claimed in claim 30 wherein during correction the intensity of each point of the first raw mask is re-evaluated by a value equivalent to $M_L-m_{PO}$ approximately and the intensity of each point of the second raw mask M is devalued by an equivalent value $m_M - m_L$ approximately.

34. A radiography device comprising:
means for emitting radiation;
means for recording or acquiring images arranged opposite the means for emitting radiation;
means for support arranged between the means for emitting radiation and the means for recording or acquisition on which an object with an area of interest to be imaged is intended to be placed wherein the device comprises:
means for acquiring a series of successive images ($I_n$) of a region of interest;
means for determining from the series of images ($I_n$) thus acquired a first mask presenting background structures and blood vessels of the region of interest;
means for determining a second mask presenting only the background structures;
means for acquiring an image ($I_L$) exhibiting at least one instrument introduced into one of the vessels of the region of interest;
means for determining an image ($I_v$) for visualizing by combination of the first and second masks and the image exhibiting the at least one instrument; and
means for displaying the image to be visualised thus determined.

* * * * *